United States Patent [19]

Weidlich et al.

[11] Patent Number: 5,103,837
[45] Date of Patent: Apr. 14, 1992

[54] IMPLANTABLE STIMULATING ELECTRODE

[75] Inventors: Erhard Weidlich, Spardorf; Waltraud Lager, Erlangen, both of Fed. Rep. of Germany

[73] Assignee: Siemens Aktiengesellschaft, Berlin & Munich, Fed. Rep. of Germany

[21] Appl. No.: 494,615

[22] Filed: Mar. 16, 1990

[30] Foreign Application Priority Data

Mar. 20, 1989 [EP] European Pat. Off. ........ 89104922.3

[51] Int. Cl.$^5$ .............................................. A61N 1/05
[52] U.S. Cl. ................................. 128/784; 128/419 P
[58] Field of Search ................................. 128/784–786, 128/419 P; 604/890.1, 891.1, 892.1

[56] References Cited

U.S. PATENT DOCUMENTS

| 4,281,668 | 8/1981 | Richter et al. | 128/784 |
| 4,304,591 | 12/1981 | Mueller | 71/93 |
| 4,474,570 | 10/1984 | Ariura et al. | 604/20 |
| 4,506,680 | 3/1985 | Stokes | 128/786 |
| 4,603,704 | 8/1986 | Mund et al. | 128/784 |
| 4,692,336 | 9/1987 | Eckenhoff et al. | 604/892.1 |
| 4,702,732 | 10/1987 | Powers et al. | 604/20 |
| 4,711,251 | 12/1987 | Stoker | 128/784 |
| 4,773,433 | 9/1988 | Richter et al. | 128/784 |
| 4,820,263 | 4/1989 | Spevak et al. | 604/20 |
| 4,869,906 | 9/1989 | Dingeldein et al. | 424/423 |

FOREIGN PATENT DOCUMENTS

| 0028122 | 5/1981 | European Pat. Off. . |
| 0047013 | 3/1982 | European Pat. Off. . |
| 0057451 | 8/1982 | European Pat. Off. . |
| WO 83/03967 | 11/1983 | European Pat. Off. . |
| 0207624 | 1/1987 | European Pat. Off. . |
| 0242672 | 10/1987 | European Pat. Off. . |
| 2613052 | 10/1977 | Fed. Rep. of Germany . |
| 2613072 | 10/1977 | Fed. Rep. of Germany . |
| 3210420 | 9/1983 | Fed. Rep. of Germany . |
| 3300668 | 7/1984 | Fed. Rep. of Germany . |
| 2842318 | 5/1985 | Fed. Rep. of Germany . |

OTHER PUBLICATIONS

Pace, vol. 11 (1988), pp. 214–219, H. Mond et al.: "The porous titanium steroid eluting electrode: A double blind study assessing the stimulation threshold effects of steroid".

Society for Biomaterials: "Transactions 13th Annual Meeting," Jun. 2–6, 1987, New York, NY, p. 52.

Primary Examiner—Lee S. Cohen
Attorney, Agent, or Firm—Kenyon & Kenyon

[57] ABSTRACT

The surface of an implantable, porous stimulating electrode particularly intended for use in pacemakers is provided with a thin coating of a hydrophilic polymer in which is embedded an anti-inflammatory steroid. The electrode reduces the postoperative increase in the stimulation threshold, as well as the growth of connective tissue, without any reduction in capacitance.

17 Claims, No Drawings

IMPLANTABLE STIMULATING ELECTRODE

The present invention relates to an implantable, porous, stimulating electrode, which is particularly intended for use in pacemakers and which contains a steroid in depository form.

The stimulation threshold of implanted stimulating electrodes is of significance in determining their efficacy. The stimulation threshold is defined to be the minimum voltage at which a stimulus is initiated or, in other words, by the minimal current at which a stimulation that leads to the excitation or contraction of the muscular system is executed. It is known that in the two weeks following implantation, conventional electrode systems of the sort which have been used for pacemaker therapy show an increase in the stimulation threshold. This is attributed to the fact that when the stimulating electrode is introduced into the tissues of the heart, the heart's muscular system is damaged, which in turn leads to the growth of connective tissue.

An example of a prior art implantable carbon electrode is set for the German Published Patent Application 28 42 318. It serves in particular as a stimulating electrode, for example as for a pacemaker. The surface of this electrode has a smooth coating of hydrophilic, ionic conducting plastic, whereby at least the surface of the plastic coating consists of material which is compatible with the body or blood. This plastic coating minimizes the energy losses occurring in the heart muscle as a result of a postoperative rise in the stimulation threshold. This is also believed to reduce clot formation at the electrode surface (which leads to increased initial and continuous stimulation thresholds).

The prior art also discloses a titanium electrode which is coated with platinum and which has a plug that lies behind the porous electrode surface. This plug is made of silicone rubber and contains a small amount (<1 mg) of the steroid dexamethasone sodium phosphate. (c.f.: Society for Biomaterials "Transactions 13th Annual Meeting", June 3–7, 1987, New York, pp 52, as well as *PACE*, vol. 11 (1988), pp. 214 to 219.) After the electrode has been exposed to body fluids (i.e. after implantation), the steroid is gradually released or eluted. This has been thought to increase the efficacy of the electrode. However, most of the steroid remains in the electrode for some time after implantation and is not quickly distributed into the surrounding tissue. Two years after implantation, 80% of the steriod remains in the electrode. One can extrapolate that 18% of the steroid would remain after 100 years.

In the prior art electrode, the availability of the steroid, i.e., its release from the electrode, is not only limited by the long time it takes, but—subject to the electrode design—it is limited locally (i.e. spatially) as well; i.e., it does not extend completely over the electrode surface. Moreover, it has been shown that as a result of adsorption at the surface of activated porous electrodes, organic silicon compounds or silicon adhesives can adversely effect the operation of the electrode, as they make the electrode surface water-repellent and thereby reduce the double-layer capacitance.

Therefore there is a need to provide an implantable stimulating electrode containing a steroid which both reduces the postoperative rise in the stimulation threshold and diminishes the growth of connective tissue, without any reduction in capacitance. Furthermore, the steroid should be uniformly delivered to the surrounding tissue within a short period of time to commence immediately after the implantation of the electrode.

SUMMARY OF THE INVENTION

The present invention fills this need by utilizing an electrode whose surface has a thin coating of a hydrophilic polymer in which is embedded an anti-inflammatory steroid.

The porous electrode surface of the electrode of the present invention is provided with a thin layer of a polymeric plastic, into which is inserted a steroid that diffuses from this layer into the adjoining tissue. In this manner, the inflammatory process is suppressed and the process by which the electrode becomes incorporated in the tissues of the heart muscle is abetted. By means of the spatially uniform, dosed release of the steroid in the region around the electrode head, the surrounding tissue is supplied with steroid uniformly over a short distance. Consequently, the growth of connective tissue is reduced and thus the postoperative rise in the stimulation threshold is lessened. The steroid is then available when needed immediately after implantation. Within as few as two days following implantation, the steroid is nearly completely eluted. As a result of the measures according to the invention, the porous surface of the electrode is protected from impurities. However, the porous electrode surface suffers no loss of capacitance.

DETAILED DESCRIPTION

The layer consisting of the hydrophilic polymer and of the steroid stored therein is generally about 2 to 50 μm thick. A preferred layer thickness is between 5 to 10 μm. Preferably, the polymer is a sulfonated polytetrafluoroethylene. Such a material, which has ionic conducting properties, can be obtained commercially under the name Nafion. Nafion, which has hydrophilic and gellike properties, is chemically and thermally stable and, in histological tests, has proven to have excellent tissue and body compatibility.

Polyvinyl alcohol, polyacrylic acid, polyamides, hydrogels and cellulose or cellulose derivatives, such as acetyl cellulose, can also be used as hydrophilic polymers. The steroid can thereby be advantageously encapsulated with the assistance of a mixture consisting of polyvinyl alcohol and polyacrylic acid.

In the present invention, cortisone is advantageously used as an anti-inflammatory steroid. Cortisone (the common name for 17α,21-dihydroxy-4-pregnene-3,11,20-trione) is one of the most important corticosteroids, i.e. adrenocortical hormones. Cortisone is numbered among the glucocorticoids and demonstrates an antiphlogistic effect that can be used therapeutically. Synthetically prepared derivatives of cortisone, such as prednisone and prednisolone, demonstrate a potentiation of the glucocorticoid effect.

Dexamethasone or one of its derivatives is preferably used as an anti-inflammatory steroid. Dexamethasone (the abbreviated name for 9α-fluoro-11β,17α,21-trihydroxy-16α-methylpregna-1,4-diene-3,20-dione) demonstrates a glucocorticoid effect and serves inter alia as an antiphlogistic agent. Dexamethasone-21-orthophosphate and its disodium salt, for example, are suitable derivatives.

The polymer, i.e. the polymeric layer can advantageously contain—apart from the steriod—a prolamine. Prolamines, which are hydrophilic, are actually plant proteins, and are, for example, found in grains and corn. Zein, the main protein from the corn gluten, is preferably used as the prolamine. Zein, which inter alia contains the amino acids glutamic acid, leucine, proline and alanine, is medicinally useful. With substances such as zein, which are further broken down in the blood or tissues of the body, one can achieve a steroid action that sets in quickly.

In the stimulating electrode of the present invention, at least the surface of the electrode head advantageously consists of surface-activated vitreous carbon or pyrocarbon (i.e. pyrolytic carbon). Implantable electrodes made of vitreous, carbon and of pyrocarbon, respectively of pyrographite, are known (German Published Patent Application 26 13 072 and German Published Patent Application 26 13 052). These types of electrodes show a high level of mechanical stability and consume little energy even in long-term operation. The relatively high polarization losses which occur thereby on smooth electrodes can be avoided when the electrodes (particularly the active region, i.e. the electrode head) are surface-activated and have a surface with a microporous structure. In this manner, then, a high double-layer capacitance is achieved.

The stimulating electrode according to the invention can also advantageously consist of an electrically conductive carrier and, in the active region, can have a porous layer consisting of a carbide, nitride or carbonitride of at least one of the metals titanium, vanadium, zirconium, niobium, molybdenum, hafnium, tantalum or tungsten. Titanium nitride is the preferred compound. This type of electrode, which is used for medical applications, is known from the German Published Patent Application 33 00 668. This electrode also possesses a high double-layer capacitance.

The surface of the stimulating electrode can be advantageously structured. This structuring can take the form of grooves, bore holes, channels or other types of depressions. As a result of modifying the electrode structure, the depository effect of the polymer/steroid coating is increased.

The following examples are presented to explain the invention in greater detail.

EXAMPLE 1

Titanium Nitride Stimulating Electrodes

Electrodes made of titanium with a porous TiN-layer deposited by sputtering (c.f.: German Published Patent Application 32 10 420) are first cleaned in isopropanol and in acetone (duration: 30 minutes each) and then treated briefly with boiling ethanol and subsequently with boiling isopropanol. The porous TiN stimulating electrodes cleaned in this manner are subsequently immersed briefly either in a nafion-dexamethasone suspension or in a nafion solution saturated with dexamethasone. The solution and suspension are prepared in the following way.

Up to 3.5% dexamethasone can be dissolved in a commercial solution of approximately 5% nafion (in a mixture of low aliphatic alcohols and water). If a larger portion of dexamethasone is introduced to the nafion solution, then one obtains a white suspension. Such a suspension is prepared for example from 10 ml of the weakly acidic nafion solution and 1 g of dexamethasone. In order not to raise the degree of acidity (in the temperature treatment of the electrodes after the coating), the nafion solution is set before the coating—and before adding the steroid—with a concentrated ammonia solution at a pH-value of 7 to 8.

The stimulating electrodes are immersed in such a solution or suspension, whereby the immersion process is repeated three times. Between the immersion processes, the electrodes are each heated to about 70° C. After the coating operation, the stimulating electrodes are subjected to a temperature treatment for drying: for one hour at each of 70° C., 90° C. and 110° C. After the drying operation, the electrodes are boiled for one hour in a physiological saline solution (0.15M NaCl, pH=7) in order to accelerate the swelling process of the nafion. Subsequently, the electrodes are also sterilized, for 20 min at 130° C. in a physiological saline solution in sealed ampules.

Impedance measurements (at 1 Hz, 100 Hz and 300 Hz) on stimulating electrodes coated in this manner show that the capacitance is not reduced by the coating. At the frequency of 1 Hz, even slightly improved capacitance values result.

When these types of stimulating electrodes are implanted in the hearts of dogs—after the settling process—within the first 50 days, stimulation thresholds of about 1 V or 1 to 1.2 V result, respectively at a pulse duration of 0.5 ms. The first value applies thereby for electrodes with a relatively small steroid content (utilization of a coating solution), the second value applies for electrodes with about 1 mg dexamethasone content (utilization of a coating suspension), respectively with an electrode surface of 0.12 cm$^2$.

EXAMPLE 2

Vitreous Carbon Stimulating Electrodes a) Nafion/Dexamethasone Coating

Activated vitreous carbon electrodes, that is electrodes with a microporous surface, which partially show a groove-shaped surface structure produced by laser treatment, are immersed three times in the nafion/dexamethasone solution described in Example 1. Between the immersion processes, the electrodes are dried under vacuum. After the coating operation, the electrodes are tempered for one hour at each of 70° C., 90° and 110° C.

b) Nafion/Dexamethasone/Zein Coating 2.5 g dexamethasone and 5 g zein are dissolved in a solvent mixture of 80 ml ethanol and 20 ml water. 2 ml of the solution obtained thereby are mixed with 2 ml of the 5% nafion solution. With this solution, activated vitreous carbon electrodes are coated and then tempered as described under (a).

c) Polyvinyl Alcohol/Polyacrylic Acid/Dexamethasone Coating

5% aqueous solutions of polyvinyl alcohol (PVA) and polyacrylic acid (PAS) are mixed in the proportions 8:1. A 0.5% solution of dexamethasone in propanol is added to the solution obtained thereby—in the proportions 1:1. With this solution, activated vitreous carbon electrodes are coated and then tempered as described under (a).

d) Acetyl Cellulose/Dexamethasone Coating

Acetyl cellulose is dissolved at room temperature in acetone to form a 5% solution. 5% dexamethasone is introduced into 2 ml of this solution. With the thus obtained solution, activated vitreous carbon electrodes are coated as described under (a) and then tempered for two hours at 50° C.

Before the implantation, the stimulating electrodes described above are also sterilized with steam or with ethylene oxide. Tests have shown that a gas sterilization using ethylene oxide does not have any negative effects, neither on the plastic coating nor on the electrode surface.

To determine capacitance, the sterilized stimulating electrodes were immersed in an electrolyte (0.15M NaCl, pH=7), and the electrode impedance was then defined as a function of time (at 40° C. and 300 Hz). It was shown thereby that the electrodes already exhibited 50% of the maximum capacitance value immediately after immersion and were thus operational. Afterwards, the capacitance increases further, because the electrolyte diffuses into the polymer coating, and after approximately two hours a stable value sets in. This stable value essentially corresponds to the maximum value that is determined on uncoated electrodes.

When these types of stimulating electrodes are implanted in sheep, a stimulation threshold of about 0.6 V is obtained right from the start (at 0.5 ms pulse duration). This value has been found not to change even after 100 days (steroid content < 1 mg, with an electrode surface of 0.12 $cm^2$).

What is claimed is:

1. An electrode, comprising:
   a) an implantable, porous, stimulating electrode having a surface bearing a thin coating of a hydrophilic polymer; and
   b) an anti-inflammatory steroid encapsulated by said polymer, whereby diffusion of said anti-inflammatory steroid after implantation into surrounding tissue prevents growth of connective tissue and thus prevents a rise in a stimulation threshold of said electrode.

2. The electrode according to claim 1, wherein the polymer is a sulfonated polytetrafluoroethylene.

3. The electrode according to claim 2, wherein the steroid is cortisone.

4. The electrode according to claim 2, wherein the steroid is dexamethasone or a derivative of this compound.

5. The electrode according to claim 1, wherein the polymer is a mixture of polyvinyl alcohol and polyacrylic acid.

6. The electrode according to claim 5, wherein the steroid is cortisone.

7. The electrode according to claim 5, wherein the steroid is dexamethasone or a derivative of this compound.

8. The electrode according to claim 1, wherein the steroid is cortisone.

9. The electrode according to claim 1, wherein the steroid is dexamethasone or a derivative of this compound.

10. The electrode according to claim 1, wherein the polymer contains a prolamine.

11. The electrode according to claim 10, wherein the prolamine is zein.

12. The electrode according to claim 1, wherein the electrode has a head portion, and wherein at least the surface of the electrode head consists of surface-activated vitreous carbon or pyro carbon.

13. The electrode according to claim 1, wherein said electrode is made of an electrically conductive carrier and, wherein the electrode further comprises a porous layer containing a carbide, nitride or carbonitride of at least one metal selected from the group consisting of titanium, vanadium, zirconium, niobium, molybdenum, hafnium, tantalum or tungsten.

14. The electrode according to claim 13 wherein the porous layer contains titanium nitride.

15. The electrode according to claim 1, wherein the electrode surface is textured.

16. The electrode according to claim 1, wherein said thin coating is between 2 to 50 micrometers thick.

17. The electrode according to claim 1, wherein said thin coating is between 5 to 10 micrometers thick.

* * * * *